United States Patent [19]

Demers

[11] 4,115,063

[45] Sep. 19, 1978

[54] METHOD FOR DETERMINING THE INORGANIC AND METALLO-ORGANIC SALT CONTENT IN AN ORGANIC SOLVENT

[75] Inventor: Donald R. Demers, Nashua, N.H.

[73] Assignee: Baird-Atomic, Inc., Bedford, Mass.

[21] Appl. No.: 786,663

[22] Filed: Apr. 11, 1977

[51] Int. Cl.$^2$ .................... G01N 33/22; G01N 21/58
[52] U.S. Cl. ........................ 23/230 M; 23/230 R; 23/230 HC
[58] Field of Search .......... 23/230 HC, 230 M, 230 R

[56] References Cited

U.S. PATENT DOCUMENTS 3,912,454   10/1975   Snyder ........................ 23/230 HC Primary Examiner—R.E. Serwin Attorney, Agent, or Firm—Morse, Altman, Oates & Bello

[57] ABSTRACT

A method for determining both the inorganic and the metallo-organic salt content in an organic solvent. A salt-free polar solvent is added to and is mixed with a sample of an organic solvent to be analyzed, producing a two-phase intermediate solution. The intermediate soluton is mixed with and is dissolved in another salt-free solvent in which the polar solvent and the organic solvent are mutually soluble, producing a one-phase final solution. The total salt content (inorganic plus metallo-organic) of the final solution is determined by conventional techniques such as, flame photometry or atomic adsorption spectrometry.

14 Claims, No Drawings

METHOD FOR DETERMINING THE INORGANIC AND METALLO-ORGANIC SALT CONTENT IN AN ORGANIC SOLVENT

BACKGROUND OF THE INVENTION

1. Field of the Invention

The present invention relates to methods for determining the total metallic salt content in organic solvents when the salt is present in both organic and inorganic forms and, more particularly, is directed towards a method for determining the sodium content in fuel oils.

2. Description of the Prior Art

Generally, sodium is present as a contaminant in fuel oils. Moreover, the sodium is usually present in diverse forms simultaneously: (1) as organo-sodium salts, for example, sodium napthanates, (2) as sodium dissolved in water that is suspended in the fuel oil, (3) as solid sodium crystals dispersed within the fuel oil, and (4) as sodium absorbed onto the surface of dirt particles or present within dirt particles in the fuel oil. The quantity of the sodium present and the relative contributions of the above forms to the total quantity present depends on the geographic source of the oil, refining process, intransient storage and handling procedures.

The total quantity of sodium in fuel oils, in whatever forms, is of considerable concern to the users of such fuel oils, particularly when they are used to power gas turbine generators. In this case, elevated sodium levels (greater than about 1 part per million ($10^{-4}\%$)) cause "sulfidation", a phenomenon in which sodium and another ever-present fuel oil contaminant, sulfur, combine in a high temperature environment of the turbine engine to form highly corrosive compounds that attack the super-alloy components of the turbine engine. Sulfidation results in a loss of turbine efficiency, less operating time between costly overhauls, and, in severe cases, engine failure. Users of such equipment can take a number of well-known corrective actions to prevent or minimize sulfidation, if they can be forewarned by a reliable, on-site method for measuring the total sodium content in their fuel oil.

The presently employed methods for determining the total sodium content in fuel oils have had varying degrees of success, principally because no single method provides a reliable measurement for all of the possible forms in which the sodium may be present in the fuel oil.

Direct aspiration of a fuel oil sample into a flame photometer is unsatisfactory in most cases due to the fact that it measures only the sodium content of the fuel oil which is present as organo-sodium salts. In many fuels, organo-sodium salts represents only a few percent of the total sodium content.

Aspiration of an ultrasonically agitated fuel oil sample into a flame photometer measures the sodium dissolved in water that is suspended in the fuel oil, the organo-sodium and the crystalline sodium. This method, however, does not measure the sodium contained in solid matter such as dirt particles. Useful application of such a method is limited to filtered or centrifuged oils.

In another method, the water extraction method, the fuel oil sample is vigorously mixed for a minute or two with approximately an equal volume of sodium-free water and the layers are allowed to separate. The aqueous layer is then aspirated into a flame photometer. This method measures crystalline sodium, sodium dissolved in water in the fuel oil, and the sodium absorbed onto but not within dirt particles in the fuel oil. It also does not measure the organo-sodium content which remains behind in the fuel oil layer.

SUMMARY OF THE INVENTION

It is an object of the present invention to provide a simple and expeditious method for determining the total metallic content in an organic solvent. In the method, a predetermined quantity of a metal-free polar solvent is added and is mixed with the organic solvent to be analyzed, producing a two-phase intermediate solution. This step dissolves the inorganic forms of the metal into the polar solvent. The two-phase solution is mixed with and is dissolved in another solvent in which the organic solvent and the polar solvent are mutually soluble, thereby producing a final one-phase solution. The total salt content of the final solution is determined by some well-known solution analysis technique such as flame photometry or atomic absorption spectrometry.

Another object of the invention is to provide a method for determining the total sodium content is fuel oils using the above approach. In the method, a predetermined quantity of sodium-free water is added and is mixed with a fuel oil sample to be analyzed, producing a two-phase intermediate solution. The two phase solution is mixed and is dissolved in a solvent in which the fuel oil and the sodium-free water are soluble, for example, a low molecular weight alcohol. This mixture is stirred vigorously until a final one-phase solution is obtained. The resultant one-phase solution is analyzed by using a solution analysis technique, such as, flame photometry and atomic absorption spectrometry.

Other objects of the present invention will in part be obvious and will in part appear hereinafter.

The invention accordingly comprises the methods, together with their steps, elements, and interrelationships that are exemplified in the following disclosure, the scope of which will be indicated in the appended claims.

DETAILED DESCRIPTION OF THE PREFERRED EMBODIMENTS

The method for determining total salt content in an organic solvent according to the present invention includes the step of adding a predetermined quantity of a polar solvent to a sample of an organic solvent to be analyzed, producing thereby an intermediate two-phase solution. By total weight, the quantity of polar solvent is in the approximate range of 0.25% to 2.0% of the organic solvent. The polar solvent must be substantially free of the salt to be measured. The two-phase mixture is then stirred briefly but vigorously. Next, a final one-phase solution is obtained by mixing and dissolving the intermediate solution in another solvent, of any appropriate volume, in which the organic solvent and the polar solvent are mutually soluble. Finally, the inorganic salt content of the final solution is determined by using, for example, flame photometry or atomic absorption spectrometry. The foregoing method is particularly suited for determining the total sodium content in fuel oils of all types, e.g., distillate, residual and even crude oils.

A specific embodiment of the invention is the analysis of total sodium content in a light distillate fuel. Here a fuel oil sample containing sodium in various forms is placed in a suitable receptacle, and approximately 1½% by weight of a polar solvent, such as sodium-free water, is added to the fuel oil sample. For samples containing particles, the added water should be acidic, at least 5% by volume, to dissolve the particles. The two-phase mixture is stirred or agitated thoroughly by hand or on a vibrator for a sufficient period of time, generally at least two minutes, in order to dissolve any crystalline salt or any inorganic sodium absorbed onto dirt particles in the sample. Next, a solvent in which the fuel oil and sodium-free water are mutually soluble, for example, certified low sodium containing 2-propanol (isopropyl alcohol), is added to the two-phase mixture. The amount of solvent added is approximately 25% by weight of the fuel sample. The concentration of sodium present in the undiluted solvent should be less than or equal to 0.2 parts per million so that, as a 20% mixture in the final solution, it is less than or equal to 0.05 parts per million, an insignificant amount compared to the levels of concern (approximately one part per million). Otherwise, a prior distillation or ion exchange step of the solvent may be necessary to reduce its sodium content to an acceptable level. Next, the mixture is stirred vigorously for a sufficiently long time, normally 30 to 40 seconds, until the added sodium-free water is dissolved. It is to be understood that in an alternative embodiment, adding the mutually soluble solvent, 2-propanol, first, followed by adding the polar solvent, water, second, is not a reliable method as only partial recovery of all the sodium in the sample may result; the sequence orginally presented is the preferred sequence. Finally, the one-phase mixture is analyzed for sodium using, preferably, the technique of flame photometry or of atomic absorption spectrometry. The backgrounds of the flames customarily used in flame photometry or atomic absorption spectrometry for the analysis of alkaline metals is affected insignificantly upon the aspiration of fuel oil into the flame. Thus, a blank solution is unnecessary. The heretofore described procedure has been used successfully with 1-propanol and n-butanol as mutually soluble solvents. It is to be understood that the present invention is not to be limited to the use of alcohols as a solvent. Any solvent which is both low in sodium and in which water and the fuel oil sample are mutually soluble is applicable to the foregoing method.

As previously indicated, the method of the present invention is not limited to fuel oil samples nor to sodium. The invention is equally applicable to: (1) other organic solvents in which the forms of the desired species to be analyzed are in the various forms mentioned earlier: organic and inorganic, undissolved particles or absorbed onto the surface of undissolved particles, (2) the analysis of other metallic species that are water soluble, or which can be rendered water soluble through means, such as, pH adjustment, or addition of a complexing agent to the polar solvent, and (3) measurement of the final single-phase solution, is not limited to flame photometry and atomic absorption spectrometry.

Since certain changes may be made in the foregoing disclosure, without departing from the scope of the invention herein involved, it is intended that all matter contained in the above description be construed in an illustrative and not in a limiting sense.

What is claimed is:

1. A method for determining inorganic and metallo-organic salt content in an organic solvent comprising the steps of:
   (a) adding a polar first solvent to a sample of an organic second solvent to be analyzed, said polar first solvent being substantially free of the inorganic salt to be measured;
   (b) mixing said polar first solvent and said organic second solvent to form an intermediate, two phase solution;
   (c) mixing and dissolving said intermediate solution in a third solvent to form a final, single phase solution, said first and second solvents being mutually soluble in said third solvent; and
   (d) measuring said inorganic salt content of said final solution by a flame atomic spectroscopy technique.

2. The method as claimed in claim 1 wherein said flame atomic spectroscopy technique for measuring said inorganic salt content in said final solution is a flame photometry technique.

3. The method as claimed in claim 1 wherein said flame atomic spectroscopy technique for measuring said inorganic salt content in said final solution is an atomic absorption spectrometry technique.

4. The method as claimed in claim 1 wherein the quantity of said polar first solvent is in the approximate range of 0.25% to 2.0% of said organic solvent.

5. A method for determining total sodium content in a fuel oil comprising the steps of:
   (a) placing a fuel oil sample containing sodium into a receptacle;
   (b) adding a polar first solvent to said receptacle;
   (c) mixing said fuel oil sample and said polar first solvent to form a two-phase mixture;
   (d) agitating said two-phase mixture for a predetermined time sufficient to dissolve any crystalline salt, dirt particles and any inorganic sodium absorbed onto dirt particles in the sample;
   (e) adding a second solvent to said two-phase mixture, said fuel oil sample and said polar first solvent mutually soluble in said second solvent;
   (f) agitating said second solvent and said two-phase mixture for a sufficiently long period in order to obtain a resultant one-phase mixture; and
   (g) measuring the resultant one-phase mixture for total sodium content.

6. The method as claimed in claim 5 wherein said step of measuring said inorganic salt content in said final solution is by flame photometry.

7. The method as claimed in claim 5 wherein said step of measuring said inorganic salt content in said final solution is by atomic absorption spectrometry.

8. The method as claimed in claim 5 wherein approximately 0.25% to 2.0% by weight of said first polar solvent is added to said receptable for forming said two-phase mixture.

9. The method as claimed in claim 8 wherein said polar first solvent is sodium-free water.

10. The method as claimed in claim 5 wherein said second solvent is certified low sodium containing 2-propanol.

11. The method as claimed in claim 10 wherein said certified low sodium containing 2-propanol added to said two-phase mixture is approximately 25% by weight of said two-phase mixture.

12. The method as claimed in claim 11 wherein said two-phase mixture and said certified low sodium containing 2-propanol is mixed for approximately 30 to 40 seconds in order to form said one-phase mixture.

13. The method as claimed in claim 5 wherein said step of agitating said two-phase mixture includes stirring said two-phase mixture for a period of approximately two minutes.

14. A method for determining metallic content in an organic solvent comprising the steps of:

(a) adding a polar first solvent to a sample of an organic second solvent to be analyzed, said polar first solvent being essentially free of the metallic content to be measured;

(b) mixing said polar first solvent and said organic second solvent to form an intermediate, two-phase solution;

(c) mixing said intermediate two-phase solution in a third solvent to reform a single phase final solution, said first and second solvents being mutually soluble in said third solvent; and (c) determining the total metallic content, both organic and inorganically bound, of said single phase final solution by an atomic spectroscopy technique.